(12) United States Patent
Akerman et al.

(10) Patent No.: US 12,410,414 B2
(45) Date of Patent: *Sep. 9, 2025

(54) PROCESS OF EXTRACTING OIL FROM THIN STILLAGE

(71) Applicant: NOVOZYMES A/S, Bagsvaerd (DK)

(72) Inventors: Michael John Akerman, Wake Forest, NC (US); Nathaniel Edward Kreel, Louisburg, NC (US); Melissa Carrie Hooss, Franklinton, NC (US); Xinyu Shen, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/167,707

(22) Filed: Feb. 10, 2023

(65) Prior Publication Data

US 2023/0303986 A1  Sep. 28, 2023

Related U.S. Application Data

(63) Continuation of application No. 16/062,769, filed as application No. PCT/US2016/067154 on Dec. 16, 2016, now Pat. No. 11,781,123.

(60) Provisional application No. 62/430,695, filed on Dec. 6, 2016, provisional application No. 62/324,107, filed on Apr. 18, 2016, provisional application No. 62/271,182, filed on Dec. 22, 2015, provisional application No. 62/271,063, filed on Dec. 22, 2015.

(51) Int. Cl.

| | | |
|---|---|---|
| C12N 9/14 | (2006.01) |
| C12N 9/16 | (2006.01) |
| C12N 9/20 | (2006.01) |
| C12N 9/26 | (2006.01) |
| C12N 9/28 | (2006.01) |
| C12N 9/34 | (2006.01) |
| C12N 9/42 | (2006.01) |
| C12N 9/44 | (2006.01) |
| C12N 9/50 | (2006.01) |
| C12P 7/06 | (2006.01) |
| C12P 19/14 | (2006.01) |
| C12P 7/64 | (2022.01) |

(52) U.S. Cl.
CPC .......... *C12N 9/14* (2013.01); *C12N 9/16* (2013.01); *C12N 9/20* (2013.01); *C12N 9/2414* (2013.01); *C12N 9/2417* (2013.01); *C12N 9/2428* (2013.01); *C12N 9/2437* (2013.01); *C12N 9/2457* (2013.01); *C12N 9/50* (2013.01); *C12P 7/06* (2013.01); *C12P 19/14* (2013.01); *C12Y 301/03008* (2013.01); *C12Y 301/04* (2013.01); *C12Y 301/04011* (2013.01); *C12Y 302/01001* (2013.01); *C12Y 302/01003* (2013.01); *C12Y 302/01004* (2013.01); *C12Y 302/01008* (2013.01); *C12Y 302/01041* (2013.01); *C12Y 304/21062* (2013.01); *C12Y 304/23023* (2013.01); *C12Y 304/24039* (2013.01); *C12P 7/64* (2013.01); *Y02E 50/10* (2013.01)

(58) Field of Classification Search
None
See application file for complete search history.

(56) References Cited

U.S. PATENT DOCUMENTS

| | | |
|---|---|---|
| 8,008,517 B2 | 8/2011 | Cantrell et al. |
| 8,535,927 B1 | 9/2013 | Jones et al. |
| 9,279,110 B2 | 3/2016 | Tang et al. |
| 9,528,128 B2 | 12/2016 | Hansen et al. |
| 9,816,112 B2 | 11/2017 | Deinhammer et al. |
| 10,351,795 B2 * | 7/2019 | Segura ............... C11B 3/003 |
| 10,597,645 B2 | 3/2020 | Jump et al. |
| 11,028,378 B2 | 6/2021 | Jump et al. |
| 11,807,889 B2 * | 11/2023 | Tassone ............ C12Y 301/00 |
| 2004/0063184 A1 | 4/2004 | Grichko |

FOREIGN PATENT DOCUMENTS

| | | |
|---|---|---|
| CN | 103608460 | 2/2014 |
| CN | 104838009 | 8/2015 |
| EP | 1905821 A1 | 6/2003 |
| WO | 2005079193 A2 | 9/2005 |
| WO | 2011/126897 A2 | 10/2011 |
| WO | 2014/074452 A1 | 5/2014 |
| WO | 2014090161 A1 | 6/2014 |
| WO | 2014/209789 A1 | 12/2014 |

(Continued)

OTHER PUBLICATIONS

Majoni et al, 2010, J Am Oil Chem Soc 88(4), 523-532.

(Continued)

*Primary Examiner* — Hope A Robinson

(74) *Attorney, Agent, or Firm* — David A. Fazzolare

(57) ABSTRACT

A process of recovering oil, comprising (a) converting a starch-containing material into dextrins with an alpha-amylase; (b) saccharifying the dextrins using a carbohydrate source generating enzyme to form a sugar; (c) fermenting the sugar in a fermentation medium into a fermentation product using a fermenting organism; (d) recovering the fermentation product to form a whole stillage; (e) separating the whole stillage into thin stillage and wet cake; (e') optionally concentrating the thin stillage into syrup; (f) recovering oil from the thin stillage and/or optionally the syrup, wherein a phospholipase is present and/or added during steps (a) to (c). Use of phospholipase for increasing oil recovery yields from thin stillage and/or syrup in a fermentation product production process.

20 Claims, 3 Drawing Sheets

Specification includes a Sequence Listing.

(56) References Cited

FOREIGN PATENT DOCUMENTS

WO 2015/116395 A1 8/2015
WO 2015/173426 A1 11/2015

OTHER PUBLICATIONS

Wang et al, 2009, J Agric Food Chem 57(6), 2302-2307.
Devos et al., 2000, Proteins: Structure, Function, and Genetics, 41, 98-107.

* cited by examiner

SEQUENCE LISTING

```
Sequence total quantity: 5
SEQ ID NO: 1              moltype = AA  length = 610
FEATURE                   Location/Qualifiers
SIGNAL                    1..16
PEPTIDE                   17..610
source                    1..610
                          mol_type = protein
                          organism = Penicillium emersonii
SEQUENCE: 1
MRVLALIAAL ATVATASAPY DKRDLAQEIW DDIKNAVDCA GCQVVLTALK GVADLGTTAL    60
VDVLTEVCNI SGKEDSDVCS GIISREGPVL DYVLQHLDIG SHTSQVICAS AFGLCQYPEV   120
RPYNLTFPKP KPNTTRPEPS GESPIQVVHF SDTHVDLSYE TGSNYNCTKP ICCRPYTAED   180
APGNTTTPCG PYGNTKCDAP LSLEESMFAA IKALNPQPAF SIYTGDVVAH DIWLVDQNEV   240
IEDLNATYDR MAGLGLVYAA IGNHDTAPVN DLPTSNIPSE YSANWTYEAL SYDFTMLTQS   300
ASAQTAANYG SYSAIYPGSY GTDLRVISYN SIFYYVDNFW AYQDPMEFDP DGQLAWLINE   360
LQEAETAGQR VWIIAHVPTG TSDHFHDYSH YFDQIVQRYE ATIAALFYGH THIDQFQISY   420
SNYSNRAFDT ATAIGYIMPS LTPTSGPPTF RVYDVDPKTF AVLDFTNYIA NISDPAFQSG   480
PSWQKYYSAK ETYGSLLSPP VTDPTAELTP AFWHNVTVAF EQDNATFQEY WARQTRGYDV   540
SSCTGSCITQ AICGLRAGDA QYNCVTPTPG FNFAKRDTSN PKQALSHVEK CEGSGLLGLL   600
RRMVADSKSS                                                         610

SEQ ID NO: 2              moltype = AA  length = 278
FEATURE                   Location/Qualifiers
SIGNAL                    1..33
PEPTIDE                   34..278
source                    1..278
                          mol_type = protein
                          organism = Bacillus thuringensis
SEQUENCE: 2
```

```
MKHHRFRTNL LSALSVSSIV ITSIIGSTQT TYAWSADAPH DPNQSTHLFI VNGAVNLVAN    60
NTDPQINKPT ALLQQWRSQW EQGLYDADHL NPYYDSGTFM SHFYDPDTQT NYAGLSYPTA   120
RQTGAKYFTI ASNDYQAGDM SDAFYNLGLS LHYFTDVTMP LHAGNISNLD HEAPGYHAKL   180
EAYAESIQNQ VTPPTAGLYN WVSPNDPELW IHQAAVQAKS VLPQVWNSDI TSWFWEAAFS   240
NYYSQQWHNA VTTPVLNQLS QAEAETAGYI DLFFRVNG                          278

SEQ ID NO: 3           moltype = AA  length = 640
FEATURE                Location/Qualifiers
SIGNAL                 1..18
PEPTIDE                19..640
source                 1..640
                       mol_type = protein
                       organism = Kionochaeata sp
SEQUENCE: 3
MRTSSILSLA LGASVAQAAV SPADVLAVVE KRVDPASGLE ARSIWDTIWD DIKSAADCTA    60
CEAVLTLLKG VAAFGDSFFV EVLTEICDLS GAEDDDVCSG VLSLEGPILA NDIRKMSIGS   120
KTSELFCITF LGLCSYPDVD AYKVPFPTAS SAATRPVSSG KDPLYVVHFS DIHIDPFYVA   180
GSASNCTKPI CCRDYTSASS PGNNDSPAGP YGDHNCDVPY SLEDSMYAAI KELVPNAAFG   240
IFTGDIVDHA VWNTSESQNI IDMNDAYSRM KSSGMLPAIF ATAGNHEASP VNAFPPPAVG   300
KESQWVYDTL ASDWSQWIGA SAASSVESQG AYSVLYGSTK LRIISLNTNM YYIENFYLYE   360
PTMETDPAGQ FAWLVSELSA AEAAGERVWI IGHMPMGLSD AFHNPSNYFD QIVNRYQATI   420
AALFFGHTHE DHFQISYSDY GAQTAANARA ISYIMPSLTP TSGHPTFRVY AVDPETFGVL   480
DATTYYADMG LASYQTAGPT WKPYYSARDA YGGLVDPPLP AGAELTPAFW HNVTAALAAN   540
QTSFDAYYAR KTRGWDVAPC TGACATAEIC ALRAARAQNN CVVPTPGVHF SKRATDEAEG   600
AHHRDECGIS VARNSLSSLV ARREALEHLE SRLVERRRAV                        640

SEQ ID NO: 4           moltype = AA  length = 515
FEATURE                Location/Qualifiers
PEPTIDE                1..515
source                 1..515
                       mol_type = protein
                       organism = Bacillus stearothermophilus
SEQUENCE: 4
AAPFNGTMMQ YFEWYLPDDG TLWTKVANEA NNLSSLGITA LWLPPAYKGT SRSDVGYGVY    60
DLYDLGEFNQ KGTVRTKYGT KAQYLQAIQA AHAAGMQVYA DVVFDHKGGA DGTEWVDAVE   120
VNPSDRNQEI SGTYQIQAWT KFDFPGRGNT YSSFKWRWYH FDGVDWDESR KLSRIYKFRG   180
IGKAWDWEVD TENGNYDYLM YADLDMDHPE VVTELKNWGK WYVNTTNIDG FRLDAVKHIK   240
FSFFPDWLSY VRSQTGKPLF TVGEYWSYDI NKLHNYITKT NGTMSLFDAP LHNKFYTASK   300
SGGAFDMRTL MTNTLMKDQP TLAVTFVDNH DTEPGQALQS WVDPWFKPLA YAFILTRQEG   360
YPCVFYGDYY GIPQYNIPSL KSKIDPLLIA RRDYAYGTQH DYLDHSDIIG WTREGVTEKP   420
GSGLAALITD GPGPGSKWMYV GKQHAGKVFY DLTGNRSDTV TINSDGWGEF KVNGGSVSVW   480
VPRKTTVSTI ARPITTRPWT GEFVRWTEPR LVAWP                              515

SEQ ID NO: 5           moltype = AA  length = 583
FEATURE                Location/Qualifiers
REGION                 1..583
                       note = Hybrid protein sequence
source                 1..583
                       mol_type = protein
                       organism = synthetic construct
SEQUENCE: 5
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFGDA SLYHPKCTID YNDQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                    583
```

PROCESS OF EXTRACTING OIL FROM THIN STILLAGE

CROSS-REFERENCE TO RELATED APPLICATIONS

This application is a continuation of U.S. application Ser. No. 16/062,769 filed Jun. 15, 2018, now U.S. Pat. No. 11,781,123, which is a 35 U.S.C. 371 national application of PCT/US2016/067154 filed Dec. 16, 2016, which claims priority or the benefit under 35 U.S.C. 119 of U.S. provisional application nos. 62/430,695 filed Dec. 6, 2016, 62/324,107 filed Apr. 18, 2016, 62/271,182 filed Dec. 22, 2015 and 62/271,063 filed Dec. 22, 2015, respectively, the contents of which are fully incorporated herein by reference.

REFERENCE TO A SEQUENCE LISTING

This application contains a Sequence Listing in computer readable form. The contents of the electronic sequence listing created on Jan. 27, 2023, named SQ_ST26.xml and 10 KB in size, is hereby incorporated by reference in its entirety.

FIELD OF THE INVENTION

The present invention relates to processes of extracting/recovering oil from thin stillage and/or syrup at the backend of a fermentation product production process based on starch-containing material.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage". The whole stillage is dewatered and separated into a solid and a liquid phase, e.g., by centrifugation. The solid phase is referred to as "wet cake" (or "wet grains") and the liquid phase (supernatant) is referred to as "thin stillage". Wet cake and thin stillage contain about 35% and 7% solids, respectively. Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup may be blended into DDG or added to the wet cake before drying to produce DDGS (Distillers Dried Grain with Solubles). An increasing number of ethanol plants extract oil from the thin stillage and/or syrup/evaporated centrate as a by-product for use in biodiesel production or other biorenewable products.

Much of the work in oil recovery/extraction from fermentation product production processes has focused on improving the extractability of the oil from the thin stillage. Effective removal of oil is often accomplished by hexane extraction. However, the utilization of hexane extraction has not seen widespread application due to the high capital investment required. Therefore, other processes that improve oil extraction from fermentation product production processes have been explored.

WO 2011/126897 (Novozymes) discloses processes of recovering oil by converting starch-containing materials into dextrins with alpha-amylase; saccharifying with a carbohydrate source generating enzyme to form sugars; fermenting the sugars using fermenting organism; wherein the fermentation medium comprises a hemicellulase; distilling the fermentation product to form whole stillage; separating the whole stillage into thin stillage and wet cake; and recovering oil from the thin stillage. The fermentation medium may further comprise a protease.

WO 2014/209789 (Novozymes) discloses processes of recovering oil after liquefaction and/or from thin stillage and/or syrup/evaporated centrate from a fermentation product production process by adding a thermostable protease to the whole stillage, thin stillage and/or syrup It is an object of the present invention to provide processes for increasing the amount of recoverable oil from fermentation product production processes.

SUMMARY OF THE INVENTION

The object of the present invention is to provide improved processes of extracting or recovering oil at the backend of a fermentation product production process, such as especially an ethanol production process.

Therefore, in the first aspect the invention relates to processes of recovering oil, comprising:
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (a) to (c).

In a preferred embodiment the phospholipase is a phospholipase C.

In an embodiment the phospholipase, in particular phospholipase C, is combined with a protease.

In an embodiment the phospholipase, in particular phospholipase C, is present and/or added during step (b) and/or step (c). Step (a) may be carried out above the initial gelatinization temperature, such as between 70-100° C., preferably between 80-90° C., such as around 85° C.

Steps (b) and (c) may be carried out simultaneously or sequentially. In embodiments steps (a), (b) and (c) are carried our simultaneously or sequentially. When steps (a), (b) and (c), or steps (b) and (c), are carried out simultaneously, the temperature is below the initial gelatinization temperature, such as between 20-60° C., preferably between 25-40° C., such as around 32° C.

The oil may according to the invention be recovered from the thin stillage and/or syrup/evaporated centrate, e.g., by extraction, such as hexane extraction, or by using another oil recovery technology well-known in the art.

In an embodiment steps (a)-(c) are carried out at a temperature below the initial gelatinization temperature. In another embodiment steps (b) and/or (c) are carried out at a temperature below the initial gelatinization temperature.

In preferred embodiments the phospholipase is selected from the group derived from Kionochaeata sp. (e.g., SEQ ID NO: 3), *Penicillium emersonii* (e.g., SEQ ID NO: 1) and *Bacillus thuringiensis* (e.g., SEQ ID NO: 2). Phospholipase C from *Penicillium emersonii* (SEQ ID NO: 1 herein) is preferred.

In another aspect the invention relates to the use of a phospholipase, in particular phospholipase C, for oil recovery from thin stillage and/or syrup at the backend of a fermentation product production process based on starch-containing material.

In an embodiment the phospholipase is combined with a surfactant.

DETAILED DESCRIPTION OF THE INVENTION

Figure 1:
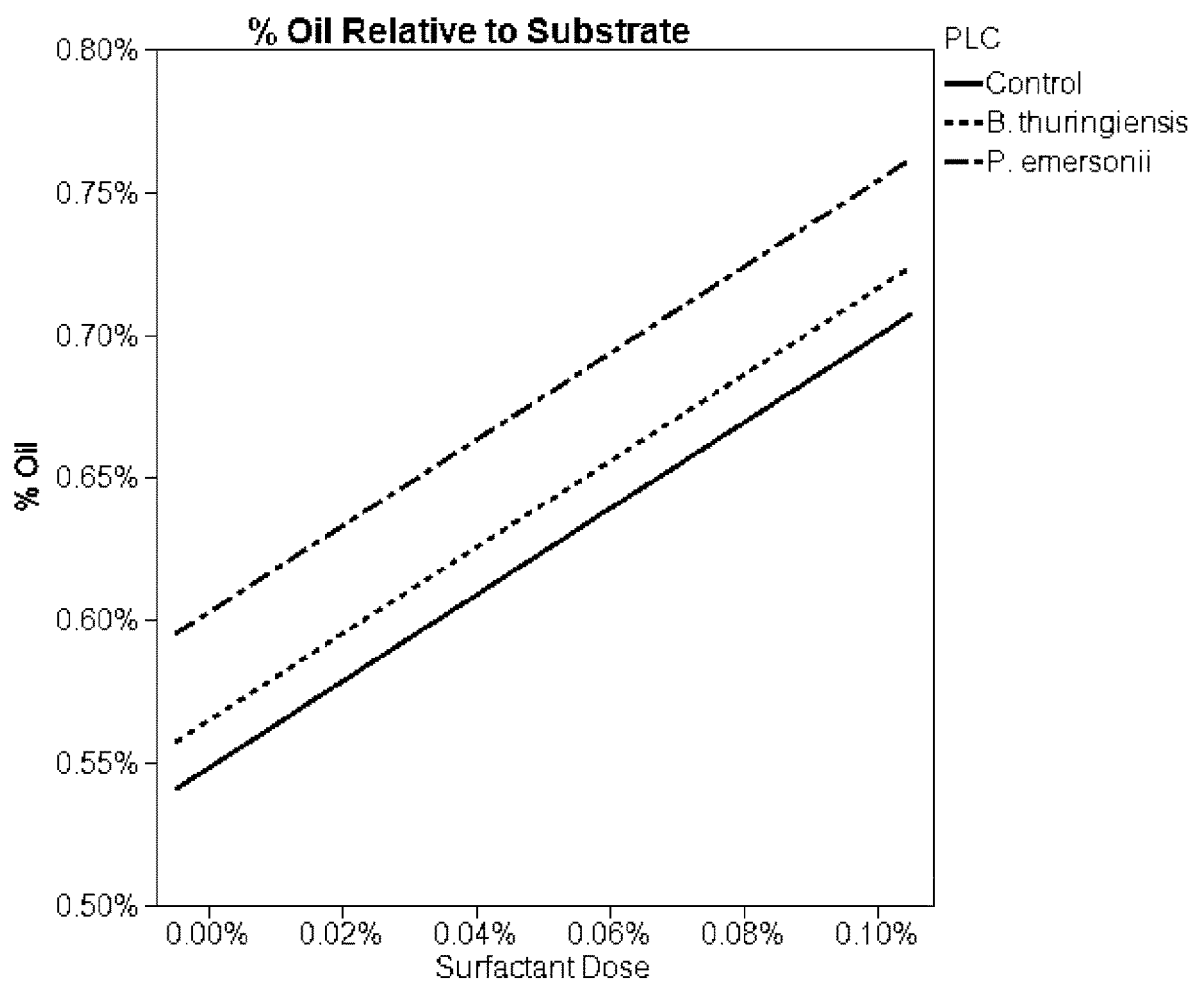
FIG. 1 shows the % oil relative to substrate dose.

The object of the present invention is to provide processes of extracting or recovering oil at the backend of fermentation product production processes, such as especially the thin stillage from an ethanol production processes.

The invention relates to using a phospholipase, in particular a phospholipase C, for recovery/extraction of oil at the back end of a fermentation product production process, in particular from thin stillage from an ethanol manufacturing process. The inventors have surprisingly found that when using a phospholipase alone, in particular phospholipase C, or in combination with a surfactant, in particular non-ionic surfactant(s), the oil recovery yield is increased. Alternatively, the amount of surfactant(s) can be reduced.

Therefore, in the first aspect the invention relates to processes of recovering oil, comprising:
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (a) to (c) (i.e., one or more of steps (a), (b) and (c)).

In an embodiment the phospholipase is present and/or added during steps (b) and/or (c).

In a preferred embodiment the phospholipase is a phospholipase C.

In an embodiment the phospholipase, in particular phospholipase C, is combined with a protease.

In an embodiment one or more surfactants, preferably non-ionic surfactants, are present and/or added. In a preferred embodiment the surfactant(s) are added and/or present in step (b) and/or step (c). The surfactant(s) is(are) preferably non-ionic surfactants, in particular selected from the group of polyethylene glycol sorbitan monooleate (e.g., TWEEN™ 80) and sorbitane monooleate (e.g., SPAN™ 80), or a mixture thereof, such as a 50:50(%) mixture thereof.

In an embodiment a protease is added during steps (a) to (c), preferably steps (b) and/or (c).

Examples of phospholipases, present and/or added in steps (a) to (c), preferably steps (b) and/or (c), includes those having the amino acid sequences of SEQ ID NO: 3 herein (e.g., from a strain of Kionochaeta); SEQ ID NO: 1 herein (e.g., from a strain of *Penicillium*); and SEQ ID NO: 2 herein (e.g., from a strain of *Bacillus*). Preferred is the phospholipase having the amino acid sequence of SEQ ID NO: 1 herein, e.g., derived from a strain of *Penicillium emersonii*.

In a preferred embodiment the phospholipase is derived, e.g., from *Penicillium*, such as the phospholipase shown in SEQ ID NO: 1 herein or one having a sequence identity thereto of at least 60%, at least 70%, at least 80%, at least 90%, at least 95%, at least 96%, at least 97%, at least 98%, at least 99%.

In an additional embodiment the phospholipase may be derived from, e.g., *Bacillus*, such as the phospholipase shown in SEQ ID NO: 2 herein or one having a sequence identity thereto of at least 60%, at least 70%, at least 80%, at least 90%, at least 95%, at least 96%, at least 97%, at least 98%, at least 99%.

In an embodiment the phospholipase may be derived from, e.g., Kionochaeta, such as the phospholipase shown in SEQ ID NO: 3 herein or one having a sequence identity thereto of at least 60%, at least 70%, at least 80%, at least 90%, at least 95%, at least 96%, at least 97%, at least 98%, at least 99%.

In an embodiment the process of recovering oil of the invention, comprises:
(a) converting a starch-containing material into dextrins with an alpha-amylase at a temperature above the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (b) and/or (c).

When step (a) is carried out as a liquefaction step at high temperatures, i.e., above the initial gelatinization temperature, such as at temperatures between 70-100° C., preferably between 80-90° C., such as around 85° C., the alpha-amylase is preferably a bacterial alpha-amylase.

In a preferred embodiment the alpha-amylase used in step (a), when the temperature in step (a) is above the initial gelatinization temperature, is a bacterial alpha-amylase.

Especially preferred are bacterial alpha-amylases derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 4 herein, in particular a *Bacillus stearothermophilus* alpha-amylase truncated, preferably to be from 485-495 amino acids long, such as around 491 amino acids long.

In a preferred embodiment the bacterial alpha-amylase is selected from the group of *Bacillus stearothermophilus* alpha-amylase variants comprising a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181+G182 compared to the amino acid sequence of *Bacillus stearothermophilus* alpha-amylase set forth as SEQ ID NO: 3 disclosed in WO 99/19467 or SEQ ID NO: 4 herein or the deletion of amino acids R179 and G180 using SEQ ID NO: 3 in WO 99/19467 or SEQ ID NO: 4 herein for numbering.

In an embodiment the bacterial alpha-amylase is selected from the group of *Bacillus stearothermophilus* alpha-amylase variants with the one of the following set of mutations:

I181*+G182*;
I181*+G182*+N193F;
preferably
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A Q89R+E129V+K177L+ R179E+Q254S+M284V; and
I181*+G182*+N193F+E129V+K177L+R179E+K220P+ N224L+S242Q+Q254S (using SEQ ID NO: 4 for numbering).

The parent *Bacillus stearothermophilus* alpha-amylase may be the one shown in SEQ ID NO: 4 herein or may be one having sequence identity thereto of at least 60%, at least 70%, at least 80%, at least 90%, at least 95%, at least 96%, at least 97%, at least 98%, at least 99%.

The *Bacillus stearothermophilus* alpha-amylase variant may be a variant of the one shown in SEQ ID NO: 4 or may be one having sequence identity thereto of at least 60%, at least 70%, at least 80%, at least 90%, at least 95%, at least 96%, at least 97%, at least 98%, at least 99%, but less than 100%.

In an embodiment the *Bacillus stearothermophilus* alpha-amylase variant has from 1-12 mutations, such as 1, 2, 3, 4, 5, 6, 7, 8, 9, 10, 11, or 12 mutations, compared to the parent alpha-amylase, especially the parent alpha-amylase shown in SEQ ID NO: 4.

In an embodiment the pH in step (a) is from 4-7, preferably 4.5-6.

Step (a) is followed by saccharification of dextrins in step (b). However, a process of the invention may further comprise a pre-saccharification step, i.e., after step (a), but before saccharification step (b), carried out for 40-90 minutes at a temperature between 30-65° C.

When step (a) is carried out at a temperature above the initial gelatinization temperature a jet-cooking step may be carried out before in step (a). Jet-cooking may be carried out at a temperature between 95-140° C. for about 1-15 minutes, preferably for about 3-10 minutes, especially around about 5 minutes.

In a preferred embodiment a process of the invention further comprises, before step (a), the steps of:
 i) reducing the particle size of the starch-containing material, preferably by dry milling;
 ii) forming a slurry comprising the starch-containing material and water.

In an embodiment the process of recovering oil of the invention comprises
 (a) converting a starch-containing material into dextrins with an alpha-amylase at a temperature below the initial gelatinization temperature;
 (b) saccharifying the dextrins using a carbohydrate source generating enzyme to form a sugar;
 (c) fermenting the sugar in a fermentation medium into a fermentation product using a fermenting organism;
 (d) recovering the fermentation product to form a whole stillage;
 (e) separating the whole stillage into thin stillage and wet cake;
 (e') optionally concentrating the thin stillage into syrup;
 (f) recovering oil from the thin stillage and/or optionally the syrup, wherein a phospholipase is present and/or added during steps (a) to (c).

In a preferred embodiment the saccharification step (b) and fermentation step (c) are carried out simultaneously, preferably at a temperature below the initial gelatinization temperature, or sequentially.

In an embodiment steps (a), (b), and (c) are carried out simultaneously. This is typically done at a temperature below the initial gelatinization temperature, i.e. raw starch hydrolysis process (RSH). However, steps (a), (b), and (c) may also be carried out sequentially at temperatures below the initial gelatinization temperature, such as between 20-60° C., preferably between 25-40° C., such as around 32° C.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C, Starch/Starke, Vol. 44 (12) pp. 461-466 (1992).

According to the invention saccharification step (b) may be carried out at a temperature from 20-75° C., preferably from 40-70° C., such as around 60° C., and at a pH between 4 and 5.

In a preferred embodiment fermentation step (c) or simultaneous saccharification and fermentation (SSF) (i.e., combined steps (b) and (c)) are carried out at a temperature between 20-60° C., preferably between 25-40° C., such as around 32° C. In an embodiment fermentation step (c) or simultaneous saccharification and fermentation (SSF) (i.e., combined steps (b) and (c)) are ongoing for 6 to 120 hours, in particular 24 to 96 hours. In an embodiment the starch-containing material converting step (a), saccharification step (b) and fermentation step (c) are carried out simultaneously or sequentially.

In an embodiment the starch-containing material converting step (a) is carried out at a temperature below the initial gelatinization temperature, preferably from 20-60° C., preferably between 25-40° C., such as around 28-36° C., such as around 32° C. In an embodiment the starch-containing material is converted to dextrins and the dextrins are saccharified to a sugar by treating the starch-containing material with an alpha-amylase and carbohydrate-source generating enzyme, in particular a glucoamylase, below the initial gelatinization temperature of the starch-containing material. In an embodiment the conversion of the starch-containing material to dextrins, the saccharification of the dextrins to sugars, and the fermentation of the sugars are carried out in a single step (i.e., raw starch hydrolysis step).

When the process of the invention is carried out as a raw starch hydrolysis process (i.e., single step process or no-cook process) the glucoamylase may preferably be derived from a strain of *Trametes*, such as a strain of *Trametes cingulata*, or a strain of *Athelia*, such as a strain of *Athelia rolfsii*. Preferred alpha-amylases used in a raw starch hydrolysis process include alpha-amylases derived from a strain *Rhizomucor*, such as a strain of *Rhizomucor pusillus*, such as a *Rhizomucor pusillus* alpha-amylase with a starch-binding domain (SBD), such as a Rhizomucorpusillus alpha-amylase with *Aspergillus nigerglucoamylase* linker and SBD. Generally the starch-containing material in raw starch hydrolysis processes (i.e., no-cook processes) are granular starch. Said granular starch may be reduced the particle size, preferably by milling, to from 0.05 to 3.0 mm, preferably 0.1-0.5 mm.

Also the sugar level, such as glucose level, may be kept below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%. The pH may be from 4-7, preferably 4.5-6.0, when conversion of the starch-containing material to dextrins, the saccharification of the dextrins to a sugar, and the fermentation of the sugar are carried out in a single step. If the process of the invention is carried out as a conventional process (i.e., step (a) is carried out as a liquefaction step at a temperature above the gelatinization temperature) the carbohydrate-source generating enzyme used in step (b) is preferably a glucoamylase derived from *Aspergillus*, preferably *A. niger*, *A. awamori*, or *A. oryzae*; or a strain of *Trichoderma*, preferably *Trichoderma reesei*; or a strain of *Talaromyces*, preferably *Talaromyces emersonii*, or a strain of Pycnoporus, or a strain of Gloephyllum.

Examples of other suitable glucoamylase can be found below in the "Glucoamylases" section below.

Generally the starch-containing material in step (a), including granular starch, contains 20-55 wt.-% dry solids, preferably 25-40 wt.-% dry solids, more preferably 30-35% dry solids.

Separation (i.e. dewatering) in step (e) may be carried out by centrifugation, preferably a decanter centrifuge, filtration, preferably using a filter press, a screw press, a plate-and-frame press, a gravity thickener or decker or any other separation technology known in the art.

The (desired) fermentation product may in an embodiment be selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. In a preferred embodiment the (desired) fermentation product is ethanol. According to the invention the desired fermentation product may be recovered by distillation. According to the invention oil may be recovered from the thin stillage and/or syrup/evaporated centrate, e.g., by extraction, such as hexane extraction.

Separating (Dewatering) Whole Stillage into Thin Stillage and Wet Cake in Step (e)

Separating whole stillage into thin stillage and wet cake in step (e), in order to remove a significant portion of the liquid/water, may be done using any suitable separation technique, including centrifugation, pressing and filtration. In a preferred embodiment the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment the separation is carried out using other conventional separation equipment such as a plate/frame filter presses, belt filter presses, screw presses, gravity thickeners and deckers, or similar equipment.

Drying of Wet Cake

After the wet cake, containing about 30-35 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS).

Fermenting Organisms

Examples of fermenting organisms used in step c) for fermenting sugars in a fermentation medium into a desired fermentation product include fungal organisms, such as especially yeast. Preferred yeast includes strains of *Saccharomyces* spp., in particular, *Saccharomyces cerevisiae*.

In one embodiment the fermenting organism is added to the fermentation medium, so that the viable fermenting organism, such as yeast, count per mL of fermentation medium is in the range from $10^5$ to $10^{12}$, preferably from $10^7$ to $10^{10}$, especially about $5\times10^7$.

Commercially available yeast includes, e.g., RED STAR™ and ETHANOL RED yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may be used as fuel which may be blended with gasoline. However, in the case of ethanol it may also be used as potable ethanol.

Recovery

Subsequent to fermentation the fermentation product, such as ethanol, may be separated from the fermentation medium, e.g., by distillation. Alternatively the desired fermentation product may be extracted from the fermentation medium by micro or membrane filtration techniques. The fermentation product may also be recovered by stripping or other method well known in the art.

Use of Protease and Phospholipase for Improving Oil Extraction

In an aspect, the invention relates to the use of a phospholipase, in particular phospholipase C, such as one described above (e.g., any of SEQ ID NOs: 1, 2 and/or 3) for increasing oil recovery yields from thin stillage and/or syrup in a fermentation product production process.

Enzymes

One or more of the following enzyme activities may be used according to the invention.

Alpha-Amylases

The process of the invention, including step (a), may be carried out using a suitable alpha-amylase. In a preferably embodiment a bacterial alpha-amylase and/or a fungal alpha-amylase may be used.

The alpha-amylase may be bacterial when step (a) is carried out as a liquefaction step at high temperatures, i.e., above the initial gelatinization temperature.

The alpha-amylase may be fungal when step (a) is carried out at a temperature below the initial gelatinization temperature, such as when steps (a), (b) and (c) are carried out as a raw starch hydrolysis (single step process or no-cook process) as described above.

Bacterial Alpha-Amylases

Examples of suitable bacterial alpha-amylases include the below mentioned. Preferred bacterial alpha-amylases used in step i) may be derived from a strain the genus *Bacillus* (sometimes referred to as *GeoBacillus*), including a strain of *Bacillus licheniformis, Bacillus amyloliquefaciens, Bacillus stearothermophilus,* or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., *Biochemical and Biophysical Research Communications*, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or SEQ ID NO: 4 herein, or deletion of amino acids R179+G180 using SEQ ID NO:3 in WO 99/19467 or SEQ ID NO: 4 herein for numbering (which reference is hereby incorporated by reference). Even more preferred are *Bacillus* alpha-amylases, especially *Bacillus stearothermophilus* alpha-amylase, which have a double deletion corresponding to delta(181-182) and optionally further comprising a N193F substitution (also denoted I181*+G182*+N193F) compared to the wild-type BSG alpha-amylase amino acid sequence set forth in SEQ ID NO:3 disclosed in WO 99/19467 or SEQ ID NO: 4 herein.

In an embodiment the *Bacillus stearothermophilus* alpha-amylase is one disclosed in WO 2011/082425, such as one selected from the group of:

I181*+G182*;
I181*+G182*+N193F;
preferably
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A+Q89R+E129V+K177L+ R179E+Q254S+M284V; and
I181*+G182*+N193F+E129V+K177L+R179E+K220P+ N224L+S242Q+Q254S (using SEQ ID NO: 4 herein for numbering).

In an embodiment the *Bacillus stearothermophilus* alpha-amylase has the following mutations: 181*+G182*+N193F+V59A+Q89R+E129V+K177L+R179E+Q254S+M284V (SEQ ID NO: 4).

The truncated *Bacillus stearothermophilus* alpha-amylase is typically naturally truncated to be about 491 amino acids long, such as from 485-495 amino acids long.

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+ A181T+N190F+I201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Commercially available bacterial alpha-amylase products and products containing alpha-amylases include TERMAMYL™ SC, LIQUOZYME™ SC, LIQUOZYME™ LpH, AVANTEC™, AVANTEC™ AMP, BAN (Novozymes A/S, Denmark) DEX-LO™, SPEZYME™ XTRA, SPEZYME™ AA, SPEZYME FRED-L, SPEZYME™ ALPHA, GC358, SPEZYME RSL, SPEZYME HPA and SPEZYME™ DELTA AA (from DuPont, USA), FUELZYME™ (Verenium, USA).

A bacterial alpha-amylase may be added in step (a) in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal alpha-amylases (EC 3.2.1.1) are preferably of filamentous fungus origin. The fungal alpha-amylase may be a fungal acid alpha-amylase.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Commercial available compositions comprising fungal alpha-amylase include FUNGAMYL™ and the acid fungal alpha-amylase sold under the trade name SP288 (available from Novozymes A/S, Denmark).

In an embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60,638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in co-pending U.S. patent application No. 60,638,614, including Fungamyl variant with catalytic domain JA1 18 and *Athelia rolfsii* SBD and SEQ ID NO: 100 in U.S. 60,638,614), *Rhizomucor pusillus* alpha-amylase with *Athelia rolfsii* AMG linker and SBD (SEQ ID NO:101 in U.S. 60,638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11,316,535), and *Meripilus giganteus* alpha-amylase with *Athelia rolfsii* glucoamylase linker and SBD (SEQ ID NO:102 in U.S. 60,638,614). Other specifically contemplated hybrid alpha-amylases are any of the ones listed in Tables 3, 4, 5, and 6 in Example 4 in U.S. application Ser. No. 11,316,535 or WO 2006/069290 (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

In a preferred embodiment the alpha-amylase is one disclosed in WO 2013/006756 including the following variants: *Rhizomucor pusillus* alpha-amylase variant having an *Aspergillus niger* glucoamylase linker and starch-binding domain (SBD) which further comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 2 in WO 2013/006756 for numbering or SEQ ID NO: 5 herein) (all incorporated by reference).

An acid alpha-amylases may according to the invention be added in an amount of 0.1 to 10 AFAU/g DS, preferably 0.10 to 5 AFAU/g DS, especially 0.3 to 2 AFAU/g DS.

Fungal alpha-amylases may be added to step (a) in a well know effective amount, preferably in the range from 0.001-1 mg enzyme protein per g DS, preferably 0.01-0.5 mg enzyme protein per g DS.

Carbohydrate-Source Generating Enzyme

According to the invention a carbohydrate-source generating enzyme, preferably a glucoamylase, is present in step (b), and may be present and/or added during step (a), saccharification step (b) and/or fermentation step (c) or simultaneous saccharification step (b) and fermentation step (c) (SSF).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used.

Specific examples include glucoamylase (being glucose generators), beta-amylase and maltogenic amylase (being maltose generators).

In a preferred embodiment the carbohydrate-source generating enzyme is a glucoamylase.

Glucoamylases

The process of the invention, including steps (b) and/or (c), may be carried out using any suitable glucoamylase. In a preferably embodiment the glucoamylase is of bacterial or fungal origin.

Contemplated glucoamylases include those from the group consisting of *Aspergillus* glucoamylases, in particular *A. niger* G1 or G2 glucoamylase (Boel et al. (1984), *EMBO J.* 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (*AgriC. Biol. Chem.* (1991), 55 (4), p. 941-949), or variants or fragments thereof. Other *Aspergillus* glucoamylase variants include variants with enhanced thermal stability: G137A and G139A (Chen et al. (1996), *Prot. Eng.* 9, 499-505); D257E and D293E/Q (Chen et al. (1995), *Prot. Eng.* 8, 575-582); N182 (Chen et al. (1994), *Biochem. J.* 301, 275-281); disulphide bonds, A246C (Fierobe et al. (1996), *Biochemistry*, 35, 8698-8704; and introduction of Pro residues in position A435 and S436 (Li et al. (1997), *Protein Eng.* 10, 1199-1204.

Other glucoamylases contemplated include glucoamylase derived from a strain of *Athelia*, preferably a strain of *Athelia rolfsii* (previously denoted *Corticium rolfsii*) glucoamylase (see U.S. Pat. No. 4,727,026 and (Nagasaka, Y. et al. (1998) "Purification and properties of the raw-starch-degrading glucoamylases from *Corticium rolfsii*, *Appl Microbiol Biotechnol* 50:323-330), *Talaromyces* glucoamylases, in particular derived from *Talaromyces emersonii* (WO 99/28448), *Talaromyces leycettanus* (US patent no. Re. 32,153), *Talaromyces duponti, Talaromyces thermophilus* (U.S. Pat. No. 4,587,215). Also contemplated are the *Trichoderma reesei* glucoamylases disclosed as SEQ ID NO: 4 in WO 2006/060062 and glucoamylases being at least 80% or at least 90% identical thereto and further the glucoamylase derived from *Humicola grisea* disclosed as SEQ ID NO: 3 in U.S. Ser. No. 10/992,187 (hereby incorporated by reference) or sequences having at least 80% or at least 90% identity thereto.

In a preferred embodiment the glucoamylase is derived from a strain of *Aspergillus*, preferably *A. niger, A. awamori,* or *A. oryzae*; or a strain of *Trichoderma*, preferably *T reesei*; or a strain of *Talaromyces*, preferably *T emersonii.*

In an embodiment the glucoamylase present and/or added during saccharification step (b) and/or fermentation step (c) is of fungal origin, preferably from a strain of Pycnoporus, or a strain of Gloephyllum. In an embodiment the glucoamylase is derived from a strain of the genus Pycnoporus, in particular a strain of Pycnoporus *sanguineus* described in WO 2011/066576 (SEQ ID NOs 2, 4 or 6), such as the one shown as SEQ ID NO: 4 in WO 2011/066576.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803.

Other contemplated glucoamylases include glucoamylase derived from a strain of *Trametes*, preferably a strain of *Trametes cingulata* disclosed in WO 2006/069289 (which is hereby incorporated by reference). Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ ULTRA, SPIRIZYME™ EXCEL, SPIRIZYME™ ACHIEVE, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.05-5 AGU/g DS (in whole stillage), especially between 0.1-2 AGU/g DS. Glucoamylase may be added in an effective amount, preferably in the range from 0.001-1 mg enzyme protein per g DS, preferably 0.01-0.5 mg enzyme protein per g dry solid (DS).

Phospholipases

Phospholipases act to hydrolyse phospholipids into their constituent fatty acids and lipophilic moieties. A preferred type of phospholipase is phospholipase C. Suitable phospholipases for use in the invention are derived from organisms, preferably from bacteria or fungi. Preferred phospholipases are derived from *Penicillium emersonii* (e.g., SEQ ID NO: 1 herein), *Bacillus thuringiensis* (e.g., SEQ ID NO: 2 herein) and Kionochaeata sp. (e.g., SEQ ID NO: 3 herein), with phospholipase C from *Penicillium emersonii* (SEQ ID NO: 1 herein) being preferred.

The invention is further summarized in the following paragraphs:

1. A process of recovering oil, comprising
    (a) converting a starch-containing material into dextrins with an alpha-amylase;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (e') optionally concentrating the thin stillage into syrup;
    (f) recovering oil from the thin stillage and/or optionally the syrup, wherein a phospholipase is present and/or added during steps (a) to (c).

2. The process of paragraph 1, wherein preferably the phospholipase is present and/or added during steps (b) and/or (c).

3. The process of paragraph 1 or 2, wherein one or more surfactants, preferably non-ionic surfactants, are present and/or added during steps (b) and/or (c).

4. The process of paragraph 3, wherein the non-ionic surfactants are selected from the group of polyethylene glycol sorbitan monooleate (e.g., TWEEN™ 80) and sorbitane monooleate (e.g., SPAN™ 80), or a mixture thereof, such as a 50:50(%) mixture.

5. The process of any of paragraph 1-4 wherein the phospholipase, present and/or added in steps (a) to (c), preferably steps (b) and/or (c), is a phospholipase C.

6. The process of any of paragraph 1-5, wherein the phospholipase, present and/or added in steps (a) to (c), preferably steps (b) and/or (c), has the amino acid sequence of SEQ ID NO: 1 herein (e.g., *Penicillium* PLC); or SEQ ID NO: 2 herein (e.g., *Bacillus*), or SEQ ID NO: 3 herein (e.g., Kionochaeta PLC), preferably where the phospholipase has the amino acid sequence of SEQ ID NO: 1 herein.

7. The process of any of paragraph 1-6, wherein the phospholipase, present and/or added in steps (a) to (c), preferably steps (b) and/or (c), is derived from *Penicillium*, such as the phospholipase shown in SEQ ID NO: 1 herein or one having a sequence identity thereto of at least 60%, at least 70%, at least 80%, at least 90%, at least 95%, at least 96%, at least 97%, at least 98%, at least 99%.

8. The process of any of paragraph 1-6, wherein the phospholipase, present and/or added in steps (a) to (c), preferably steps (b) and/or (c), is derived from *Bacillus*, such as the phospholipase shown in SEQ ID NO: 2 herein or one having a sequence identity thereto of at least 60%, at least 70%, at least 80%, at least 90%, at least 95%, at least 96%, at least 97%, at least 98%, at least 99%.

9. The process of any of paragraph 1-6, wherein the phospholipase, present and/or added in steps (a) to (c), preferably steps (b) and/or (c), is derived from Kionochaeta, such as the phospholipase shown in SEQ ID NO: 3 herein or one having a sequence identity thereto of at least 60%, at least 70%, at least 80%, at least 90%, at least 95%, at least 96%, at least 97%, at least 98%, at least 99%.

10. The process of recovering oil of any of paragraph 1-9, comprising
    (a) converting a starch-containing material into dextrins with an alpha-amylase at a temperature above the initial gelatinization temperature;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (e') optionally concentrating the thin stillage into syrup;
    (f) recovering oil from the thin stillage and/or optionally the syrup, wherein a phospholipase is present and/or added during steps (b) and/or (c).

11. The process of paragraph 10, wherein the temperature in step (a) is above the initial gelatinization temperature, such as at a temperature between 80-90° C., such as around 85° C.

12. The process of paragraph 10 or 11, wherein saccharification step (b) and fermentation step (c) are carried out simultaneously.

13. The process of any of paragraph 10-12, wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 4 herein, in particular the *Bacillus stearothermophilus* alpha-amylase is truncated, preferably to have from 485-495 amino acids, such as around 491 amino acids.

14. The process of recovering oil of any of paragraphs 1-9, comprising
    (a) converting a starch-containing material into dextrins with an alpha-amylase at a temperature below the initial gelatinization temperature;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (e') optionally concentrating the thin stillage into syrup;
    (f) recovering oil from the thin stillage and/or optionally the syrup, wherein a phospholipase is present and/or added during steps (a) to (c).

15. The process of paragraph 14, wherein saccharification step (b) and fermentation step (c) are carried out simultaneously, preferably at a temperature below the initial gelatinization temperature, or sequentially.

16. The process of paragraph 14 or 15, wherein steps (a), (b) and (c) are carried out simultaneously or sequentially at a temperature below the initial gelatinization temperature.

17. Use of a phospholipase for increasing oil recovery yields from thin stillage and/or syrup in a fermentation product production process.

18. The use of paragraph 17, wherein the phospholipase is a phospholipase C.

19. The use of any of paragraph 17-18, wherein the phospholipase has the amino acid sequence of SEQ ID NO: 1 herein; SEQ ID NO: 2 herein; or SEQ ID NO: 3 herein, preferably where the phospholipase has the amino acid sequence of SEQ ID NO: 1 herein.

20. The use of any of paragraph 17-19, wherein the phospholipase is derived from *Penicillium*, such as the phospholipase shown in SEQ ID NO: 1 herein or one having a sequence identity thereto of at least 60%, at least 70%, at least 80%, at least 90%, at least 95%, at least 96%, at least 97%, at least 98%, at least 99%.

21. The use of any of paragraph 17-20, wherein the phospholipase is derived from *Bacillus*, such as the phospholipase shown in SEQ ID NO: 2 herein or one having a sequence identity thereto of at least 60%, at least 70%, at least 80%, at least 90%, at least 95%, at least 96%, at least 97%, at least 98%, at least 99%.

22. The use of any of paragraph 17-21, wherein the phospholipase is derived from Kionochaeta, such as the phospholipase shown in SEQ ID NO: 3 herein or one having a sequence identity thereto of at least 60%, at least 70%, at least 80%, at least 90%, at least 95%, at least 96%, at least 97%, at least 98%, at least 99%.

23. The use of any of paragraph 17-22, wherein the phospholipase is combined with one or more surfactants, preferably non-ionic surfactants.

24. The use of paragraph 23, wherein the non-ionic surfactants are selected from the group of polyethylene glycol sorbitan monooleate (e.g., TWEEN™ 80) and sorbitane monooleate (e.g., SPAN™ 80), or a mixture thereof, such as a 50:50(%) mixture.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods

Alpha-Amylase 369 ("AA369"): *Bacillus stearothermophilus* alpha-amylase with the mutations: I181*+G182*+N193F+V59A+Q89R+E129V+K177L+R179E+Q254S+M284V truncated to be around 491 amino acids long (SEQ ID NO: 4 herein).

Glucoamylase SA ("GSA") comprises a blend comprising *Talaromyces emersonii* glucoamylase disclosed in WO99/28448, *Trametes cingulata* glucoamylase disclosed as SEQ ID NO: 2 in WO 06/69289, and *Rhizomucor pusillus* alpha-amylase with *Aspergillus niger* glucoamylase linker and SBD disclosed as SEQ ID NO: 5 herein with the following substitutions: G128D+D143N (activity ratio AGU:AGU:FAU(F): approx. 30:7:1).

PLC Pe: *Penicillium emersonii* shown in SEQ ID NO: 1 herein

PLC Bt: *Bacillus thuringiensis* shown in SEQ ID NO: 2 herein

Tween™ 80 is a non-ionic surfactant (polyethylene glycol sorbitan monooleate) purchased from Fisher Scientific as a Fisher Chemical product, CAS: 9005-65-6, Catalog No. T164-500.

SPAN™ 80 is a non-ionic surfactant (Sorbitane monooleate) purchased from Fisher Scientific as a Sigma-Aldrich product, CAS: 1338-43-8, Catalog No. NC0765791.

Determination of Alpha-Amylase Activity

1. Phadebas™ Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units. In this absorbance range there is linearity between activity and absorbance (Lambert-Beer law). The dilution of the enzyme must therefore be adjusted to fit this criterion. Under a specified set of conditions (temperature, pH, reaction time, buffer conditions) 1 mg of a given alpha-amylase will hydrolyze a certain amount of substrate and a blue colour will be produced. The measured absorbance is directly proportional to the specific activity (activity/mg of pure alpha-amylase protein) of the alpha-amylase in question under the given set of conditions.

2. Alternative Method

Alpha-amylase activity is alternatively determined by a method employing the PNP-G7 substrate. PNP-G7 which is an abbreviation for p-nitrophenyl-alpha,D-maltoheptaoside, which is a blocked oligosaccharide that can be cleaved by an endo-amylase. Following the cleavage, the alpha-glucosidase included in the kit digest the substrate to liberate a free PNP molecule which has a yellow colour and thus can be measured by visible spectophometry at wavelength Lambda=405 nm (400-420 nm). Kits containing PNP-G7 substrate and alpha-glucosidase are manufactured by Bohringer-Mannheim (cat. No. 1054635).

To prepare the substrate one bottle of substrate (BM 1442309) is added to 5 ml buffer (BM1442309). To prepare the alpha-glucosidase one bottle of alpha-glucosidase (BM 1462309) is added to 45 ml buffer (BM1442309). The working solution is made by mixing 5 ml alpha-glucosidase solution with 0.5 ml substrate.

The assay is performed by transforming 20 microL enzyme solution to a 96 well microtitre plate and incubating at 25° C. 200 microL working solution, 25° C. is added. The solution is mixed and pre-incubated 1 minute and absorption is measured every 15 seconds over 3 minutes at OD 405 nm.

The slope of the time dependent absorption-curve is directly proportional to the specific activity (activity per mg enzyme) of the alpha-amylase in question under the given set of conditions.

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| Substrate | Soluble starch |
|---|---|
| Temperature | 37° C. |
| pH | 4.7 |
| Reaction time | 7-20 minutes |

A detailed description of Novozymes' method for determining KNU and FAU is available on request as standard method EB-SM-0009.02/01. Determination of acid alpha-amylase activity (AFAU)

Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S).

The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 ⅓ (Novo method for the determination of fungal alpha-amylase). In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

Alpha-amylase

Starch+Iodine→Dextrins+Oligosaccharides

40° C., *pH* 2.5

Blue/violet *t*=23 sec. Decolouration

Standard Conditions/Reaction Conditions: (Per Minute)

Substrate: starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: Lambda=590 nm
Enzyme concentration: 0.025 AFAU/mL
Enzyme working range: 0.01-0.04 AFAU/mL Further details can be found in standard method document EB-SM-0259.02/01 available on request from Novozymes A/S, which folder is hereby incorporated by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum soluble.

A folder EB-SM-0009.02/01 describing this analytical method in more detail is available upon request to Novozymes A S, Denmark, which folder is hereby included by reference.

Glucoamylase and Alpha-Glucosidase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: acetate | 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Protease Activity (AU)

Dimethyl casein (DMC) is hydrolyzed by the proteolytic enzyme to small peptides. The primary amino groups formed in this process react with trinitrobenzene sulphonic acid (TNBS) forming a coloured complex. This colour development is monitored in situ so the change in absorption per time unit can be calculated. This figure is a measure of the reaction rate and thus of the enzyme activity.

| Reaction conditions for the DMC reaction | |
|---|---|
| Temperature: | 50° C. |
| pH: | 8.3 |
| Wavelength: | 405 nm |
| Reaction time: | 8 min. |
| Measuring time: | 2 min. |
| Enzyme concentration range: | 0.072-0.216 mAU/ml. |

The activity is determined relative to an enzyme standard.

The assay is further described in standard method document EB-SM-0218.02/02 available upon request from Novozymes A/S, Denmark.

EXAMPLES

Example 1

Extracting Free Oil Using Phospholipase and Surfactant

The purpose of this experiment is to measure the free corn oil yield increase realized through the use of one of two PLC enzymes, either *Penicillium emersonii* PLC (PLC Pe) or *Bacillus thuringiensis* PLC (PLC Bt), and a dose response of a surfactant blend consisting of 50% TWEEN@80 and 50% SPAN® 80 with or without PLC.

Method

Fermentation: Industrially mash liquefied with Alpha-Amylase 369 was stored frozen. One liter of mash was thawed for approximately 2 hours prior to starting this study. The dry solids content of the mash was measured on a Mettler-Toledo moisture balance, with a resulting value of 33.70% DS. The mash was prepared to 1000 ppm urea and 3 mg/L penicillin using solutions of 200 g/L urea and 1 g/L penicillin, respectively, and adjusted to pH 5 using 40% v/v $H_2SO_4$. Approximately 27 g of each prepared mash was pipetted into each of 45 pre-weighed 50 mL centrifuge tubes, which had holes drilled in the top.

The PLCs used were *Penicillium emersonii* (PLC Pe) and *Bacillus thuringiensis* PLC (PLC Bt). The surfactant used was a blend consisting of 50% w/w TWEEN™ 80 and 50% w/w SPAN™ 80, based on surfactant optimization reported by Wang, et al (Fang, L., Wang, T., & Lamsal, B. (2015). Synergistic effect of surfactants and silica nanoparticles on oil recovery from condensed corn distillers solubles (CODS). Industrial Crops & Products, 553. doi:10.1016/j.indcrop.2015.09.031).

RED STAR™ yeast (*Saccharomyces cerevisiae*) was rehydrated, with 2.75 g of yeast placed in 50 mL of 32° C. tap water for 30 minutes.

TABLE

Treatments tested

| Treatment | Glucoamylase | Glucoamylase Dose (AGU/gDS) | PLC | PLC Dose (µg/gDS) | Surfactant Dose (% w/w) |
|---|---|---|---|---|---|
| 1 | GSA | 0.6 | Control | 0 | 0.00% |
| 2 | GSA | 0.6 | Control | 0 | 0.03% |
| 3 | GSA | 0.6 | Control | 0 | 0.05% |
| 4 | GSA | 0.6 | Control | 0 | 0.08% |
| 5 | GSA | 0.6 | Control | 0 | 0.10% |
| 6 | GSA | 0.6 | P. emersonii | 20 | 0.00% |
| 7 | GSA | 0.6 | P. emersonii | 20 | 0.03% |
| 8 | GSA | 0.6 | P. emersonii | 20 | 0.05% |
| 9 | GSA | 0.6 | P. emersonii | 20 | 0.08% |
| 10 | GSA | 0.6 | P. emersonii | 20 | 0.10% |
| 11 | GSA | 0.6 | B. thuringiensis | 20 | 0.00% |
| 12 | GSA | 0.6 | B. thuringiensis | 20 | 0.03% |
| 13 | GSA | 0.6 | B. thuringiensis | 20 | 0.05% |
| 14 | GSA | 0.6 | B. thuringiensis | 20 | 0.08% |
| 15 | GSA | 0.6 | B. thuringiensis | 20 | 0.10% |

TABLE

Enzymes

| Name | stock conc. | Units | Dilution (X) | expt. conc | units |
|---|---|---|---|---|---|
| P. emersonii | 24 | mg/mL | 6.5 | 3.67 | µg/uL |
| B. thuringiensis | 11 | mg/g | 3.1 | 3.54 | µg/uL |
| Glycoamylase SA (GSA) | 1234 | AGU/g | 10.0 | 0.12 | AGU/uL |

Enzyme doses were calculated via the following equation, or similar:

$$\text{Enz. dose (ml)} = \frac{\text{Final enz. dose}(AGU/g\,DS) \times \text{Mash weight}(g) \times \text{Solid content}(\%DS)}{\text{Conc. enzyme (mg}\,AGU/\text{ml)}}$$

TABLE

Enzyme Dosing

| Tube # | PLC | PLC Dose (µl) | GSA Dose (µl) | Yeast (µl) | H2O |
|---|---|---|---|---|---|
| 1 | Control | 0.0 | 44.1 | 250 | 75.3 |
| 2 | Control | 0.0 | 43.9 | 250 | 72.6 |
| 3 | Control | 0.0 | 43.8 | 250 | 71.0 |
| 4 | Control | 0.0 | 43.7 | 250 | 69.6 |
| 5 | Control | 0.0 | 43.7 | 250 | 69.8 |
| 6 | Control | 0.0 | 43.5 | 250 | 67.5 |
| 7 | Control | 0.0 | 43.9 | 250 | 72.6 |
| 8 | Control | 0.0 | 44.0 | 250 | 73.7 |

TABLE-continued

Enzyme Dosing

| Tube # | PLC | PLC Dose (µl) | GSA Dose (µl) | Yeast (µl) | H2O |
|---|---|---|---|---|---|
| 9 | Control | 0.0 | 44.0 | 250 | 74.4 |
| 10 | Control | 0.0 | 44.0 | 250 | 74.2 |
| 11 | Control | 0.0 | 43.7 | 250 | 70.7 |
| 12 | Control | 0.0 | 43.7 | 250 | 70.6 |
| 13 | Control | 0.0 | 43.6 | 250 | 69.0 |
| 14 | Control | 0.0 | 44.1 | 250 | 74.7 |
| 15 | Control | 0.0 | 43.9 | 250 | 73.1 |
| 16 | P. emersonii | 48.9 | 43.7 | 250 | 20.7 |
| 17 | P. emersonii | 49.5 | 44.2 | 250 | 27.0 |
| 18 | P. emersonii | 49.3 | 44.0 | 250 | 24.4 |
| 19 | P. emersonii | 49.1 | 43.8 | 250 | 22.4 |
| 20 | P. emersonii | 48.9 | 43.6 | 250 | 20.5 |
| 21 | P. emersonii | 49.1 | 43.8 | 250 | 22.5 |
| 22 | P. emersonii | 49.0 | 43.7 | 250 | 21.3 |
| 23 | P. emersonii | 48.9 | 43.6 | 250 | 20.5 |
| 24 | P. emersonii | 49.2 | 43.9 | 250 | 24.0 |
| 25 | P. emersonii | 49.4 | 44.1 | 250 | 26.1 |
| 26 | P. emersonii | 49.1 | 43.8 | 250 | 21.9 |
| 27 | P. emersonii | 48.6 | 43.4 | 250 | 17.0 |
| 28 | P. emersonii | 49.0 | 43.8 | 250 | 21.9 |
| 29 | P. emersonii | 49.3 | 44.0 | 250 | 24.6 |
| 30 | P. emersonii | 49.3 | 44.0 | 250 | 24.2 |
| 31 | B. thuringiensis | 50.8 | 43.8 | 250 | 20.0 |
| 32 | B. thuringiensis | 50.8 | 43.7 | 250 | 19.7 |
| 33 | B. thuringiensis | 51.0 | 43.9 | 250 | 21.5 |
| 34 | B. thuringiensis | 51.1 | 44.0 | 250 | 23.0 |
| 35 | B. thuringiensis | 50.8 | 43.8 | 250 | 20.2 |
| 36 | B. thuringiensis | 50.9 | 43.8 | 250 | 20.8 |
| 37 | B. thuringiensis | 51.3 | 44.1 | 250 | 24.7 |
| 38 | B. thuringiensis | 51.4 | 44.2 | 250 | 25.9 |
| 39 | B. thuringiensis | 51.0 | 43.9 | 250 | 21.5 |
| 40 | B. thuringiensis | 50.9 | 43.8 | 250 | 20.5 |
| 41 | B. thuringiensis | 52.0 | 44.8 | 250 | 32.4 |
| 42 | B. thuringiensis | 50.9 | 43.8 | 250 | 21.1 |
| 43 | B. thuringiensis | 50.4 | 43.4 | 250 | 15.7 |
| 44 | B. thuringiensis | 51.2 | 44.1 | 250 | 23.6 |
| 45 | B. thuringiensis | 50.9 | 43.8 | 250 | 20.7 |

Water was dosed into each sample such that the total added volume of enzyme and water was 621 µL/27 g sample. All samples were dosed with 250 µL of rehydrated yeast solution and vortexed. Each sample was weighed when all samples had been dosed. The samples were placed in a shaking incubator set at 32° C. for 64 hours.

Free Oil Assay: The sample tubes are then processed on an assay validated to measure the free extractable oil. This assay consists of dosing the tubes with surfactant, incubating at 65° C. for 10 minutes, and centrifuging at 3000×g for 10 minutes. The tubes are then carefully rinsed with hexane multiple times in order to extract hexane from the top surface (free) oil layer. The hexane wash consists of five rinses: 10 mL, 5 mL, 5 mL, 2.5 mL, 2.5 mL. The collected hexane/oil mixture for each tube is then evaporated on a Buchi Multivapor to isolate the corn oil. The weight of the corn oil is then taken and normalized to the starting material.

Figure 2:
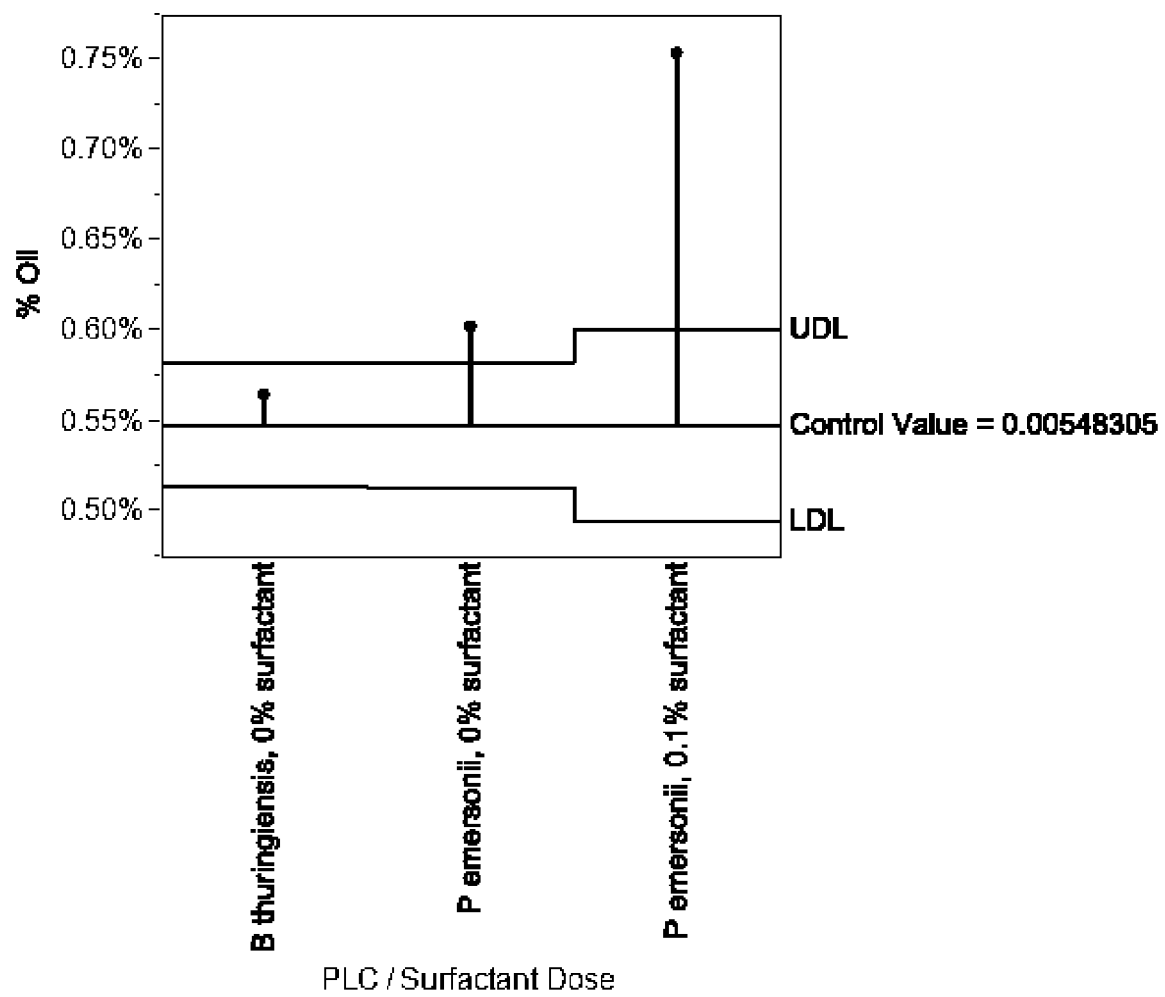
FIG. 2 shows the % oil vs PLC/Surfactant dose.
Figure 3:
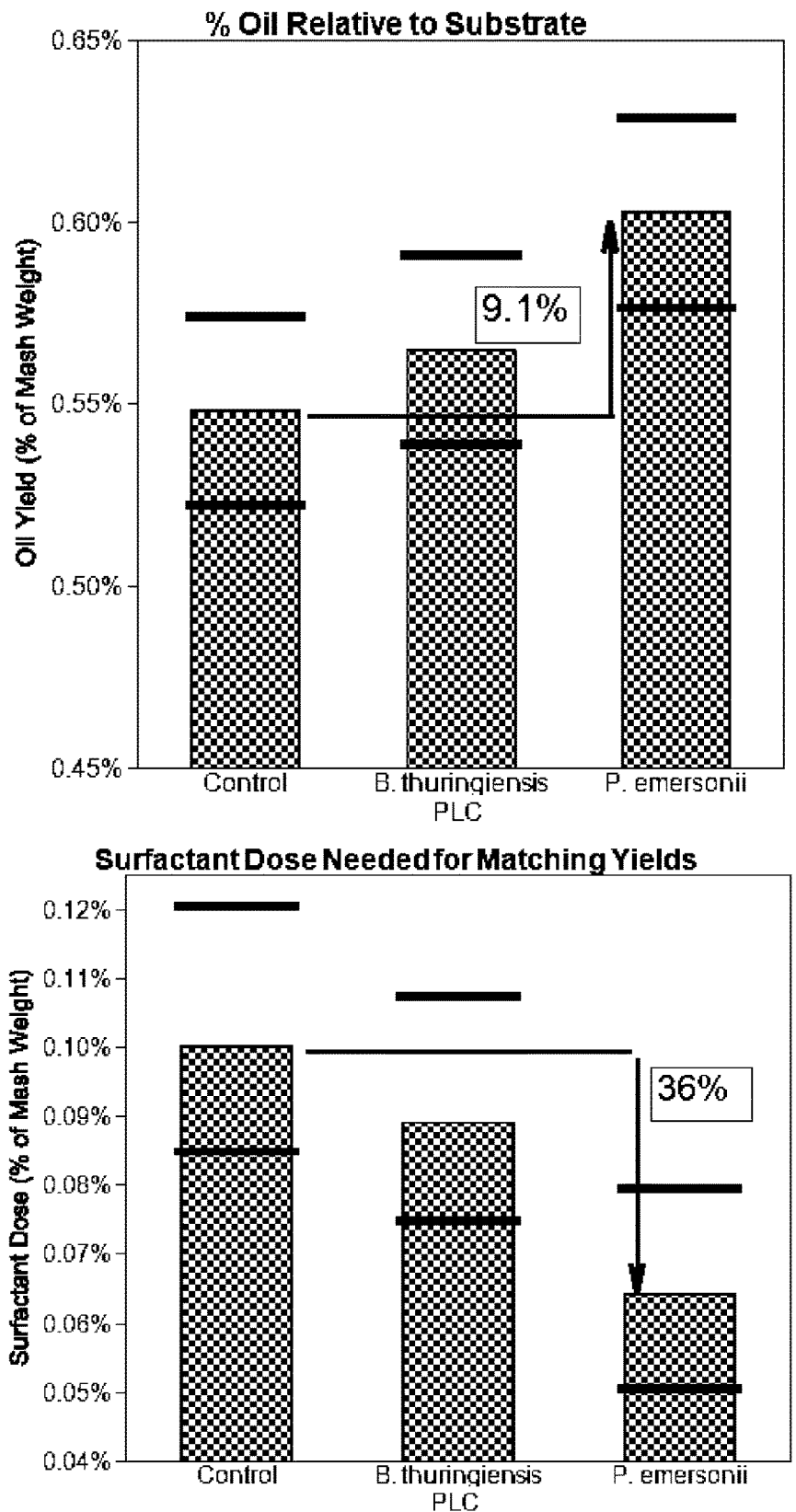
FIG. 3 shows the oil yield for PLC Pe, PLC Bt and a Control and surfactant dose needed for matching yields.

The results are shown in FIGS. 1-3. Statistical analysis, performed in JMP 12.0.1 using the Fit Model platform, revealed that the addition of surfactant linearly increased oil yields for the control and both PLC treatments. In this model, the P. emersonii PLC also significantly improved oil yields over the control, increasing free oil by 9.1%.

One thing to note is that the slope of oil yield relative to surfactant is the same for both PLCs and for the control.

The increase in oil yield due to the addition of P. emersonii PLC was found to be significant relative to the control, as previously mentioned (FIG. 2).

Without using any surfactant, the free oil yield is increased by 9.1% relative to the control by application of the P. emersonii PLC (see FIG. 3).

Alternatively, by adding the P. emersonii PLC, the required surfactant dose to maintain the top measured yield with no PLC can be reduced by 36% (FIG. 3).

CONCLUSION

The use of PLC can increase free oil yields by 9.1%, or reduce the necessary surfactant dose by 36%.

The invention claimed is:

1. A process of recovering oil, comprising:
    (a) converting a starch-containing material into dextrins with an alpha-amylase at a temperature above the initial gelatinization temperature;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (f) optionally concentrating the thin stillage into syrup; and
    (g) recovering oil from the thin stillage and/or optionally the syrup,
    wherein a phospholipase C having at least 80% sequence identity to the amino acid sequence of SEQ ID NO: 2 is present and/or added during steps (b) and/or (c).

2. The process of claim 1, wherein the phospholipase C is added during step (b).

3. The process of claim 1, wherein the phospholipase C is added during step (c).

4. The process of claim 1, wherein the saccharifying step (b) and fermenting step (c) are performed as a simultaneous saccharification and fermentation (SSF) and the phospholipase C is added during SSF.

5. The process of claim 1, wherein a surfactant is present and/or added during steps (b) and/or (c).

6. The process of claim 5, wherein the surfactant is selected from the group consisting of: polyethylene glycol, sorbitan monooleate, sorbitane monooleate, and mixtures thereof.

7. The process of claim 1, wherein the phospholipase C has at least 90% sequence identity to the amino acid sequence of SEQ ID NO: 2.

8. The process of claim 1, wherein the phospholipase C has at least 95% sequence identity to the amino acid sequence of SEQ ID NO: 2.

9. A process of recovering oil, comprising:
    (a) converting a starch-containing material into dextrins with an alpha-amylase at a temperature below the initial gelatinization temperature;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (f) optionally concentrating the thin stillage into syrup; and
    (g) recovering oil from the thin stillage and/or optionally the syrup,
    wherein a phospholipase C having at least 80% sequence identity to the amino acid sequence of SEQ ID NO: 2 is present and/or added during steps (a), (b) and/or (c).

10. The process of claim 9, wherein steps (b) and (c) are carried out simultaneously.

11. The process of claim 10, wherein the phospholipase C is added during step (a).

12. The process of claim 11, wherein a surfactant is present and/or added during step (a).

13. The process of claim 10, wherein the phospholipase C is added during step (b) and/or step (c).

14. The process of claim 13, wherein a surfactant is present and/or added during step (b) and/or step (c).

15. The process of claim 9, wherein steps (a) to (c) are carried out simultaneously and the phospholipase is added during steps (a) to (c).

16. The process of claim 15, wherein a surfactant is present and/or added during steps (a), (b) and/or (c).

17. The process of claim 9, wherein the phospholipase C has at least 90% sequence identity to the amino acid sequence of SEQ ID NO: 2.

18. The process of claim 9, wherein the phospholipase C has at least 95% sequence identity to the amino acid sequence of SEQ ID NO: 2.

19. The process of claim 9, wherein the phospholipase C comprises the amino acid sequence of SEQ ID NO: 2.

20. The process of claim 1, wherein the phospholipase C comprises the amino acid sequence of SEQ ID NO: 2.

* * * * *